United States Patent [19]
Fruehauf

[11] Patent Number: 5,840,507
[45] Date of Patent: Nov. 24, 1998

[54] METHODS FOR CANCER PROGNOSIS AND DIAGNOSIS

[75] Inventor: John Fruehauf, Tustin, Calif.

[73] Assignee: Oncotech, Inc., Irvine, Calif.

[21] Appl. No.: 843,008

[22] Filed: Apr. 11, 1997

Related U.S. Application Data

[60] Provisional application No. 60/041,311 Mar. 19, 1997.

[51] Int. Cl.[6] .................................................. G01N 33/53
[52] U.S. Cl. ........................ 435/7.23; 435/7.1; 435/7.2; 530/387.7; 530/389.7
[58] Field of Search ........................... 435/7.1, 7.2, 7.23; 530/387.7, 389.7

[56] References Cited

PUBLICATIONS

Iwaya et al Jpn Cancer Research vol. 82 835–840, Jul. 1991.
Zabrenetzky et al Int J Cancer VOI 59 191–195, 1994.
Gasparini et al Journal of Clinical Oncology VOI 13 No. 3 765–782, Mar. 1995.
Grossfeld et al Proceedings of the American Urological Association vol. 155 Supplement 688A Abstract 1508, May 1996.
Bevilacqua et al Breast Cancer Research and Treatment vol. 36 205–217, 1995.
Boring et al., (1992), *Clin. J. Cancer,* 42: pp. 19–38.
Mansour et al., (1989), *N. Engl. J. Med.,* 320: 485–490.
Osbourne et al., (1992), *J. Clin. Oncol.,* 679–682.
Allegra et al., (1979), *Cancer Treat. Rep.,* 63: 1271–1277.
Von Rosen et al., (1989), *Breast Cancer Res. Treat.,* 13: pp. 23–32.
Fisher et al., (1992), *J. Natl. Cancer. Inst.,* 11: 152–258.
Clark et al., (1994), *N.Engl. J. Med.,* 320: pp. 627–633.
Fisher et al., (1993), *Cancer Medicine,* $3^{rd}$ Edition, Holland et al., pp. 1706–1774.
Early Breast Cancer Trialists Collaborative Group (1992), *Lancet,* 339: pp. 1–15.
The Ludwig Breast Cancer Study Group (1989), *N. Engl. J. Med.,* 320: 491–496.
Gasparini et al., (1993), *J. Natl. Cancer Inst.,* 85: 1206–1219.

*Primary Examiner*—Sheela Huff
*Assistant Examiner*—Julie E Reeves
*Attorney, Agent, or Firm*—McDonnell Boehnen Hulbert & Berghoff

[57] ABSTRACT

The invention provides methods for prognosis, diagnosis, staging and disease progression in human cancer patients related to expression levels of a variety of immunohistochemical and genetic markers associated with poor cancer prognosis, and in particular those markers related to tumor invasiveness, metastasis and spread. The invention also provides methods using a predictive index for prognosis of cancer patients for metastasis, recurrence and relapse of neoplastic disease. The methods of the invention are useful for making clinical decisions on cancer treatment, surveillance and surgical intervention.

4 Claims, 7 Drawing Sheets

METHODS FOR CANCER PROGNOSIS AND DIAGNOSIS

This application is a continuation in part of provisional application Ser. No. 60/041,311, filed 19 Mar. 1997.

BACKGROUND OF THE INVENTION

1. Field of the Invention

The invention relates to cancer diagnosis and treatment, and specifically to the determination of a predictive index for prognosis of cancer patients for metastasis, recurrence and relapse of neoplastic disease. The invention relates to the determination of a variety of immunohistochemical and genetic markers associated with poor cancer prognosis, and in particular those markers related to tumor invasiveness, metastasis and spread. The invention particularly relates to the use of certain markers associated with tumor invasiveness, metastasis and spread to provide a prognostic index for making clinical decisions on cancer treatment, surveillance and surgical intervention.

2. Summary of the Related Art

Cancer remains one of the leading causes of death in the United States. Clinically, a broad variety of medical approaches, including surgery, radiation therapy and chemotherapeutic drug therapy are currently being used in the treatment of human cancer (see the textbook *CANCER: Principles & Practice of Oncology*, 2d Edition, De Vita et al., eds., J. B. Lippincott Company, Philadelphia, Pa., 1985). However, it is recognized that such approaches continue to be limited by a fundamental inability to accurately predict the likelihood of metastasis and tumor recurrence or the most efficacious treatment regime for minimizing the occurrence of these negative outcomes.

The discovery and clinical validation of markers for cancer of all types which can predict prognosis, likelihood of invasive or metastatic spread is one of the major challenges facing oncology today. In breast cancer, for example, 70% of the approximately 186,00 annual cases present as lymph node negative; however, 30% of these cases will recur after local therapy (mastectomy or "lumpectomy") (Boring et al., 1992, *Clin. J. Cancer* 42: 19–38). Although adjuvant chemotherapy has been demonstrated to improve survival in node negative breast cancer patients (Mansour et al., 1989, *N. Engl. J. Med.* 320: 485–490), it remains uncertain how to best identify patients whose risk of disease recurrence exceeds their risk of significant therapeutic toxicity (Osbourne, 1992, *J. Clin. Oncol.* 10: 679–682).

Current approaches to answer these questions stratify node negative breast cancer on the basis of primary tumor size, pathological grade, DNA S-phase fraction (SPF) and steroid hormone receptor status (Allegra et al., 1979, *Cancer Treat. Rep.* 63: 1271–1277; Von Rosen et al., 1989, *Breast Cancer Res. Treat.* 13: 23–32; Fischer et al., 1992, *J. Natl. Cancer Inst.* 11: 152–258; Clark et al., 1994, *N. Engl. J. Med.* 320: 627–633). For example, moderately and well-differentiated tumors <1 cm in size are thought to require only local excision regardless of receptor status, while such tumors from 1 to 3 cm in size that express normal levels of hormone receptor are treated with hormone therapy (Fischer et al., 1993, in *Cancer Medicine*, 3d ed., Holland et al., eds., Philadelphia: Lea & Febiger, pp. 1706–1774). On the other hand, patients with tumors larger than 2 cm that are poorly differentiated and/or hormone receptor negative are treated with adjuvant chemotherapy (Early Breast Cancer Trialistic Collaborative Group 1992, *Lancet* 339: 1–15; The Ludwig Breast Cancer Study Group 1989, *N. Engl. J. Med.* 320: 491–496). However, therapeutic indications are much less clearly defined for patients having moderately differentiated tumors of 1 to 3 cm in size where the hormone receptor status is borderline or unknown (Gasparini et al., 1993, *J. Natl. Cancer Inst.* 85: 1206–1219). Deciding the most appropriate therapy for this group of patients, comprising about 70,000 women annually, would benefit from the development of validated prognostic analysis. Similar prognostic tools are needed in most other forms of cancer.

Thus, there is a need in this art for developing methods for making clinical decisions on adjuvant therapy, tumor surveillance and the likelihood of disease progression based on validated tumor markers statistically correlated with tumor invasiveness, metastasis and recurrence.

SUMMARY OF THE INVENTION

The present invention provides methods for predicting a disease course in a human cancer patient. The invention also provides a prognostic (risk) index for making predictions about disease progression and prognosis, and for determining the proper course of treatment for an individual patient using the index to grade the patient's tumor and estimate their chances for survival.

In a first aspect the invention provides a method for making a prognosis of disease course in a human cancer patient. The method comprises the following steps. First, a sample of a tumor from the human cancer patient is obtained. Then, the levels of three tumor markers in the tumor sample are determined, and compared with levels of these markers in a control, non-invasive, non-metastatic tumor sample of the same type. The tumor markers tested are nuclear localization of p53 protein (which is used as an indicator of p53 mutation), thrombospondin 1 expression, and the extent of microvascularization in the tumor sample (as a measure of angiogenesis in the sample). In the practice of the invention, a poor prognosis, that is, a prognosis of the likelihood of further neoplastic, particularly metastatic, disease, is made when the level of nuclear localization of p53 in the tumor sample is greater than the level of nuclear localization of p53 protein in the non-invasive, non-metastatic tumor sample; the level of thrombospondin 1 expression in the tumor sample is less than the level of thrombospondin 1 expression in the non-invasive, non-metastatic tumor sample; and the extent of microvascularization in the tumor sample is greater than the extent of microvascularization in the non-invasive, non-metastatic tumor sample.

In a preferred embodiment, the determination of a poor prognosis is made when the level of nuclear localization in the tumor sample is from about twofold to about tenfold, more preferably about fivefold, greater than the level of nuclear localization of p53 protein in the non-invasive, non-metastatic tumor sample.

In a preferred embodiment, the determination of a poor prognosis is made when the level of thrombospondin 1 expression in the tumor sample is from about twofold to about tenfold, more preferably about fivefold, less than the level of thrombospondin 1 expression in the non-invasive, non-metastatic tumor sample.

In a preferred embodiment, the determination of a poor prognosis is made when the extent of microvascularization in the tumor sample is from about twofold to about tenfold, more preferably about sixfold, greater than the extent of microvascularization in the non-invasive, non-metastatic tumor sample.

In a more preferred embodiment, the determination of a poor prognosis is made when the level of nuclear localization of p53 in the tumor sample is from about twofold to about tenfold greater than the level of nuclear localization of p53 protein in the non-invasive, non-metastatic tumor sample, and the level of thrombospondin 1 expression in the tumor sample is from about twofold to about tenfold less than the level of thrombospondin 1 expression in the non-invasive, non-metastatic tumor sample and the extent of microvascularization in the tumor sample is from about twofold to about tenfold greater than the extent of microvascularization in the non-invasive, non-metastatic tumor sample. Most preferably, the level of nuclear localization of in the tumor sample is from about fivefold greater than the level of nuclear localization of p53 protein in the non-invasive, non-metastatic tumor sample, the level of thrombospondin 1 expression in the tumor sample is from about fivefold less than the level of thrombospondin 1 expression in the non-invasive, non-metastatic tumor sample and the extent of microvascularization in the tumor sample is from about sixfold greater than the extent of microvascularization in the non-invasive, non-metastatic tumor sample in determining a poor prognosis for a cancer patient.

In preferred embodiments, the levels of nuclear localization of p53, thrombospondin 1 expression and the extent of microvascularization are determined by immunohistochemical staining and detected by microscopy.

The invention also provides methods wherein the results of the determination of the levels of nuclear localization of p53, thrombospondin 1 expression, and the extent of microvascularization are used to prepare a prognostic or "risk" index for making a prognostic determination. In this aspect of the invention, a prognostic index is prepared comprising the product of the percentage of cells in the tumor sample that are positive for nuclear localization of p53 protein and one plus the intensity of immunohistochemical staining; the product of the percentage of cells in the tumor sample that are positive for microvascularization and one plus the intensity of immunohistochemical staining; and the product of the percentage of cells in the tumor sample that are positive for thrombospondin 1 expression and one plus the intensity of immunohistochemical staining. In calculating these products, the intensity of staining is assigned a value of 0 for staining equal to a negative control, a value of 1 for weak staining greater than the negative control, a value of 2 for moderate staining intensity, a value of 3 for staining intensity equal to a positive control, and a value of 4 for staining intensity greater than the positive control. The calculated products of each of the tumor marker determinations are then weighted on a scale of from +1 to −4, and the index is produced as the sum of the weighted products for nuclear localization of p53, thrombospondin 1 expression and microvascularization. In the practice of the invention, a prognosis of a likelihood of further neoplastic, particularly metastatic, disease is made when this sum is less than about −5.

In additional embodiments, the prognostic index is produced by preparing a weighted scale of expression levels of the tumor markers related to progression observed in a representative sample of a particular tumor type, wherein the different values in the weighted scale are related to increased invasiveness or metastatic spread in the representative sample.

The methods of the invention are also provided for identifying a human cancer patient at risk for additional neoplastic disease, for staging malignant disease in a human cancer patient and assessing the relative risk of metastatic disease versus the risk of toxicity (such as leukocytopenia, for example) from chemotherapeutic treatment.

The methods of the invention are provided for prognosis of disease course in a cancer patient suffering from any specific cancer of any tissue of origin. In preferred embodiments, the cancer is breast cancer, prostate cancer or melanoma.

Specific preferred embodiments of the present invention will become evident from the following more detailed description of certain preferred embodiments and the claims.

DETAILED DESCRIPTION OF THE PREFERRED EMBODIMENTS

Figure 1A:
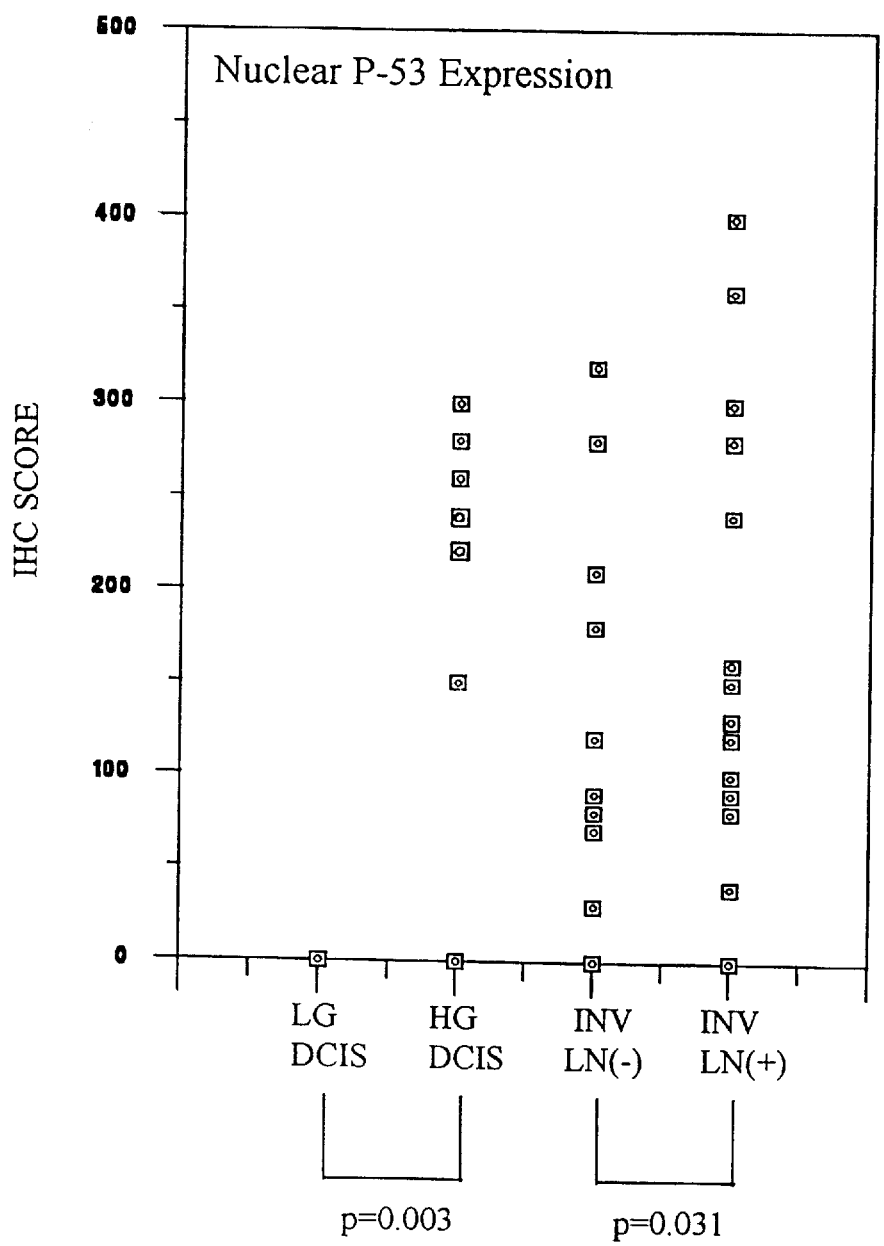
FIGS. 1A, 1B and 1C are histograms of the intensity of tumor marker staining versus tumor histology for four histological subsets described in Example 1. The p values indicate significance of the observed differences between samples of different histologies, determined using paired, one-tail t-test analysis.

The present invention provides a method for making a prognosis about disease course in a human cancer patient. For the purposes of this invention, the term "prognosis" is intended to encompass predictions and likelihood analysis of disease progression, particularly tumor recurrence, metastatic spread and disease relapse. The prognostic methods of the invention are intended to be used clinically in making decisions concerning treatment modalities, including therapeutic intervention, diagnostic criteria such as disease staging, and disease monitoring and surveillance for metastasis or recurrence of neoplastic disease.

The methods of the invention are preferably performed using human cancer patient tumor samples, most preferably samples preserved, for example in paraffin, and prepared for histological and immunohistochemical analysis.

The invention also provides an index for use with the methods of the invention to relate three tumor markers (p53 nuclear accumulation, thrombospondin-1 expression and microvascularization) with disease progression, particularly invasiveness and metastatic spread. The indices of the invention can be prepared as described herein for any tumor type, provided that there is available a representative cohort of samples of the tumor type having varying degrees of tumor invasiveness and metastatic spread, to enable the production of a weighted scale of expression levels of the three tumor markers. Preferably, the size of the cohort is sufficiently large to enable statistical analyses to verify the significance of differences in tumor marker expression for disease progression.

Indices as provided by the invention can also be constructed using any relevant tumor marker associated with disease progression, again provided that there is available a representative cohort of samples of the tumor type having varying degrees of tumor invasiveness and metastatic spread, to enable the production of a weighted scale of expression levels of the three tumor markers. Preferably, the size of the cohort is sufficiently large to enable statistical analyses to verify the significance of differences in tumor marker expression for disease progression. Additional tumor markers can be added to the three tumor markers used in the practice of this invention, or other tumor markers can replace any of the markers described herein, if such markers meet the proviso discussed above.

The methods of the invention are practiced by determining expression levels of the three preferred tumor markers (p53 nuclear accumulation, thrombospondin-1 expression and microvascularization) in a human cancer patient sample. In preferred embodiments, expression levels are determine immunohistochemically. However, expression levels can be determined using any appropriate and convenient method. For example, in situ polymerase chain reaction and in situ nucleic acid hybridization methods for determining expression levels of TSP-1 fall within the methods of the invention. Additionally, site-specific mutation analysis, including sequence analysis or mutant allele-specific amplification of mutant p53, can be used for determining expression levels of mutant p53 in a tumor sample. Similarly, any method for detecting microvascularization, including any method of specific staining, fall within the ambit of the methods of the present invention. Detection methods are chosen appropriate for the labeling or identification of any of the three tumor markers used in the practice of the invention.

In a preferred embodiment, the present invention uses immunohistochemical methods for detecting expression levels of the tumor markers of the invention. In the practice of the invention, antibodies or antisera, preferably polyclonal antisera, and most preferably monoclonal antibodies specific for each marker are used to detect expression levels, using anti-p53, anti-TSP-1 and anti-CD31 antibody immunostaining. Detection of these antibodies can be realized by direct labeling of the antibodies themselves, with labels including a radioactive label such as $^3H$, $^{14}C$, $^{35}S$, $^{125}I$ or $^{131}I$, a fluorescent label, a hapten label such as biotin, or an enzyme such as horse radish peroxidase or alkaline phosphatase. Alternatively, unlabeled primary antibody is used in conjunction with labeled secondary antibody, comprising antisera, polyclonal antisera or a monoclonal antibody specific for the primary antibody. In a preferred embodiment, the primary antibody or antisera is unlabeled, the secondary antisera or antibody is conjugated with biotin and enzyme-linked streptavidin is used to produce visible staining for histochemical analysis.

Detection and quantitation of the tumor markers is provided using methods appropriate for the staining or other detection method used. In preferred embodiments, immunohistochemically stained sections of a tumor sample are analyzed microscopically, most preferably by light microscopy of a sample stained with a stain that is detected in the visible spectrum, using any of a variety of such staining methods and reagents known to those with skill in the art. Most preferably the methods of the invention are practiced by those with skill in the histological arts, but embodiments of the invention provided to permit relatively unskilled technicians to properly interpret tumor marker results are also within the scope of the methods provided.

The following Examples are intended to further illustrate certain preferred embodiments of the invention and are not limiting in nature.

EXAMPLE 1

Tumor Progression/Prognosis Analysis for Breast Cancer

Nuclear localization of p53 protein, thrombospondin 1 expression levels and extent of microvascularization were determined immunohistochemically as follows.

Tumor blocks from breast cancer patients were obtained from Western Medical Center and H. Lee Moffitt Cancer Center and examined independently by two pathologists to confirm the diagnosis for tumor type and stage. Representative sections of each tumor sample were chosen on the basis of pathological examination for immunohistochemical staining. Tissue sections 5 microns in thickness were cut and prepared on slides using standard histological preparation techniques. Since paraffin sections were used, slides were first deparaffinized using Histoclear (Biogenics, California). Antigens were exposed for immunohistochemical staining by pronase digestion (for CD31 detection) and by microwave boiling (for p53 and thrombospondin 1 (TSP-1) detection) using antigen recovery solution (Biogenics). Slides were then incubated in a solution of 3% hydrogen peroxide in distilled water at room temperature for 10 min, then rinsed briefly with water. Slides were then incubated for 10 min at room temperature using 100 µL goat serum as blocking buffer. Excess blocking buffer was removed from the slides by shaking, and the slides then incubated with primary antibody at room temperature for 30 min. The primary antibodies used in these assays were: antibody DO1 for p53 (obtained from Santa Cruz Biotech, Santa Cruz, Calif.); antibody clone 12 for TSP-1 (Immunotech, Inc., Westbrook, Me.); and an endothelial cell-specific antibody reactive with the cell surface antigen CD31 for microvascularization (Dako, Carpenteria, Calif.). Slides were rinsed twice with phosphate buffered saline (PBS) for 5 min after primary antibody incubation.

For detection of primary antibody binding, tissue sections were then incubated with biotinylated goat antimouse immunoglobulin for 20 min at room temperature in a humidified chamber (70–100% relative humidity). Slides were rinsed twice with PBS after this incubation, and then treated with a solution of peroxidase-conjugated streptavidin for 20 min at room temperature. After being rinsed again with PBS, the slides were incubated in a solution of 3,3'-diaminobenzidine for 3 min at room temperature. Slides were rinsed with PBS for 5 min, exposed to hematoxylin for 1 min, rinsed with water for 10 min, dehydrated in an ascending ethanol series, to cleared with xylene, mounted and viewed by light microscopy.

Microscopic analyses were performed at 200× magnification as follows. The malignant cells on the slide were counted, and the number of stained cells and staining intensity determined. Each slide was scored independently by two pathologists. Scoring of staining intensity was relative to the following scale:

0=staining intensity equal to the negative control

1=staining intensity weak but greater than negative control

2=staining intensity moderate (more than negative control, but less than positive control)

3=staining intensity strong, equal to positive control

4=staining intensity greater than positive control.

Control slides used for comparison were paraffin-embedded MCF-7 40F cells (ATCC #HTB-22) for p53 and TSP-1. Microvascularization controls were paraffin-embedded tumor specimens showing high reactivity with anti-CD31 antibody.

Alternatively, TSP-1 expression was determined using image analysis (IA) techniques. Slides immunohistochemically stained for detection of TSP-1 expression as described above were analyzed using a CAS 200 image analysis system (Cell Analysis Systems, Lombard, Ill.) to quantitate the staining intensity of TSP-1 marker positive cells as described (see Figge et al., 1991, Amer. J. Pathol. 139: 1213–1221 and Esteban et al., 1993, Amer. J. Clin. Pathol. 99: 32–38). This analytical method uses a two-color system to sample image data using 2 solid-state video cameras, each with its own optical filter, mounted on a light microscope. Video signals are sent to an image capture board, which samples and digitizes the analog signal. The digital value of the signal sample is proportional to the amplitude of the video signal and is stored in an interactive computer. Measurements are obtained from calibrated conversion of pixel information from the video image.

For IA of TSP-1 expression in breast cancer tumor samples, the instrument was set at threshold values optimized to distinguish between cell membrane, nuclear and cytosolic portions of the stained image, and the zero pixel set-point adjusted using a tumor section stained with an isotype-matched irrelevant (i.e., unrelated) antibody. At least 10 fields of positive area on the slide were scanned for each tumor specimen. Video values were converted to the product of the positive areas and positively-stained areas, expressed as optical density (O.D.) Units using instrument software. Antigen preservation control was evaluated using vimentin staining (1:200 antibody dilution, obtained from Dako, Carpenteria, Calif.). The results of IA were consistent with results obtained by visual analysis of the stained tumor sections.

The values of staining intensity related to "positive" or "negative" predicted outcomes were determined based on univariate analysis of the markers on survival, using a training subset (n=42) for which survival data were known. Immunohistochemistry (IHC) scores were assigned based on the product of the percentage of cells positive in the sample times (1+intensity of staining), using the staining intensity scale described above. Tissue sections with immunodetectably nuclear p53 observed in more than 5% of the cells with 2+staining intensity (corresponding to an IHC value >15) were considered positive. (It is noted that the presence of nuclear-located p53 is used as a marker for mutant p53, consistent with the difference in cellular location of mutant p53 versus wildtype known in the prior art (Hall & Lane, 1994, J. Pathol. 172: 1–4). For IA of TSP-1 expression, positive sections were determined to have a value of >30 O.D. For angiogenesis, microvessels were counted in the region of greatest vessel density over at least 10 fields; samples designated as positive had >70 vessels per field. Statistics, including Fischer's exact test and unpaired one-tailed t test were performed using a software program (GraphPad Software, v2.05, San Diego, Calif.) to compare values for each markers' incidence and intensity of expression as a function of histological progression.

The results of these assays are shown in Tables I and II. Table I presents the results for the tested markers based on a dichotomy of invasive versus non-invasive ductal breast carcinoma (as determined by pathological examination of breast tumor samples and registry information provided for each sample), while Table II shows the difference in staining patterns observed for the 4 histological subsets studied. These results show that highly significant changes in all three of the tested markers were observed in the transition from non-invasive to invasive disease. The frequency of nuclear p53 localization and microvascularization were found to be increased (>5-fold) significantly (p<0.0001) in invasive tumor tissue, while the frequency of thrombospondin 1 expression decreased (>5-fold) significantly (p<0.0001) in these tumor samples.

When the tumor samples are further distinguished based on four (rather than two) subsets of morphological and histochemical criteria, additional differences were detected. As shown in Table II, frequency of nuclear localization of p53 increased significantly (p=0.006) in a comparison between low-grade and high-grade ductal carcinoma in situ (DCIS), even though both subsets are non-invasive. In these assays, nuclear p53 staining was not detected in any of the low-grade DCIS samples, while 31% (6/22) of the high-grade DCIS samples showed positive staining.

For the transition between high-grade (but non-invasive) DCIS to frankly invasive ductal carcinoma with negative lymph nodes, only the decline in TSP-1 expression was significant (p<0.002), with the frequency of TSP-1 expression declining from 82% (18/22 samples) to 32% (6/19 samples). In addition, the transition from invasive ductal carcinoma without lymph node metastasis to invasive disease accompanied by lymph node metastasis showed significant changes in p53 nuclear localization, TSP-1 expression and microvascularization. The incidence of samples with p53 nuclear localization in tumor samples comprising metastatic cancer increased from 47% (9/19 samples) to 82% (14/17 samples) (p=0.041), the incidence of samples with high microvessel counts increased from 53% (10/19 samples) to 100% (17/17 samples) (p=0.001), and the incidence of samples with pronounced TSP-1 staining decreased from 32% (6/19 samples) in tumor without lymph node involvement to 0% (0/17 samples) in tumors associated with metastasis-positive lymph nodes (p=0.02).

TABLE I

Marker Profile: Invasive versus Non-invasive Ductal Breast Carcinoma

|  | Percent Positive Markers Studied: | | |
| --- | --- | --- | --- |
| Tumor Type | p53 | TSP-1 | Microvasc. |
| Non-invasive (n = 48) | 12 | 83 | 12 |
| Invasive (n = 36) | 64 | 17 | 75 |
| P value* | <0.0001 | <0.0001 | <0.0001 |

* = P value determined by unpaired one-tailed t-test.

TABLE II

Marker Profile of Breast Carcinoma Progression

|  | Percent Positive Markers Studied: | | |
| --- | --- | --- | --- |
| Tumor Type | p53 | TSP-1 | Microvasc. |
| Low-grade DCIS[1] (n = 26) | 0 | 89 | 4 |
| High-grade DCIS (n = 36) | 31* | 82 | 23 |
| Invasive - LN(−)[2] (n = 10) | 47 | 32* | 53 |
| Invasive - LN(+)[3] (n = 17) | 82* | 0 | 100* |

Figure 1B:
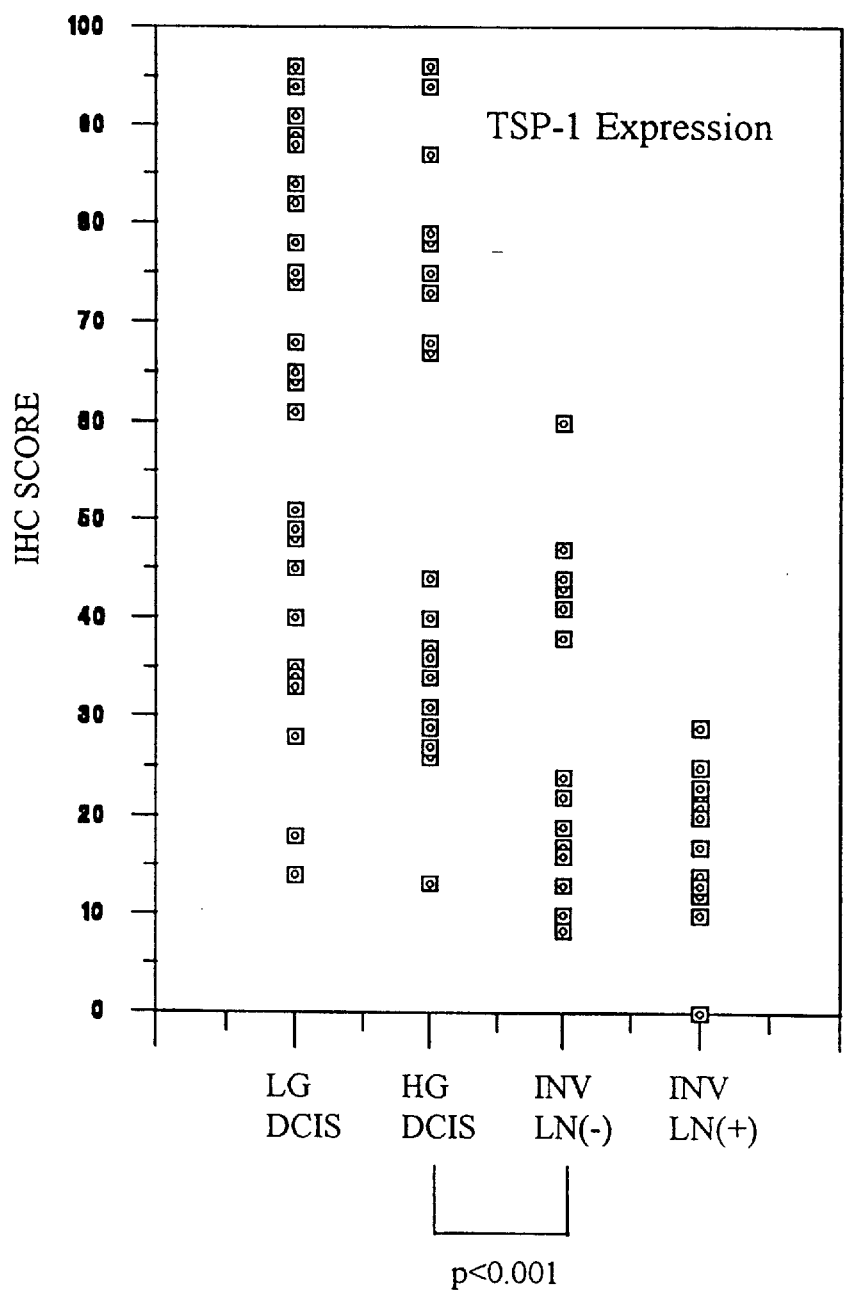
Figure 1C:
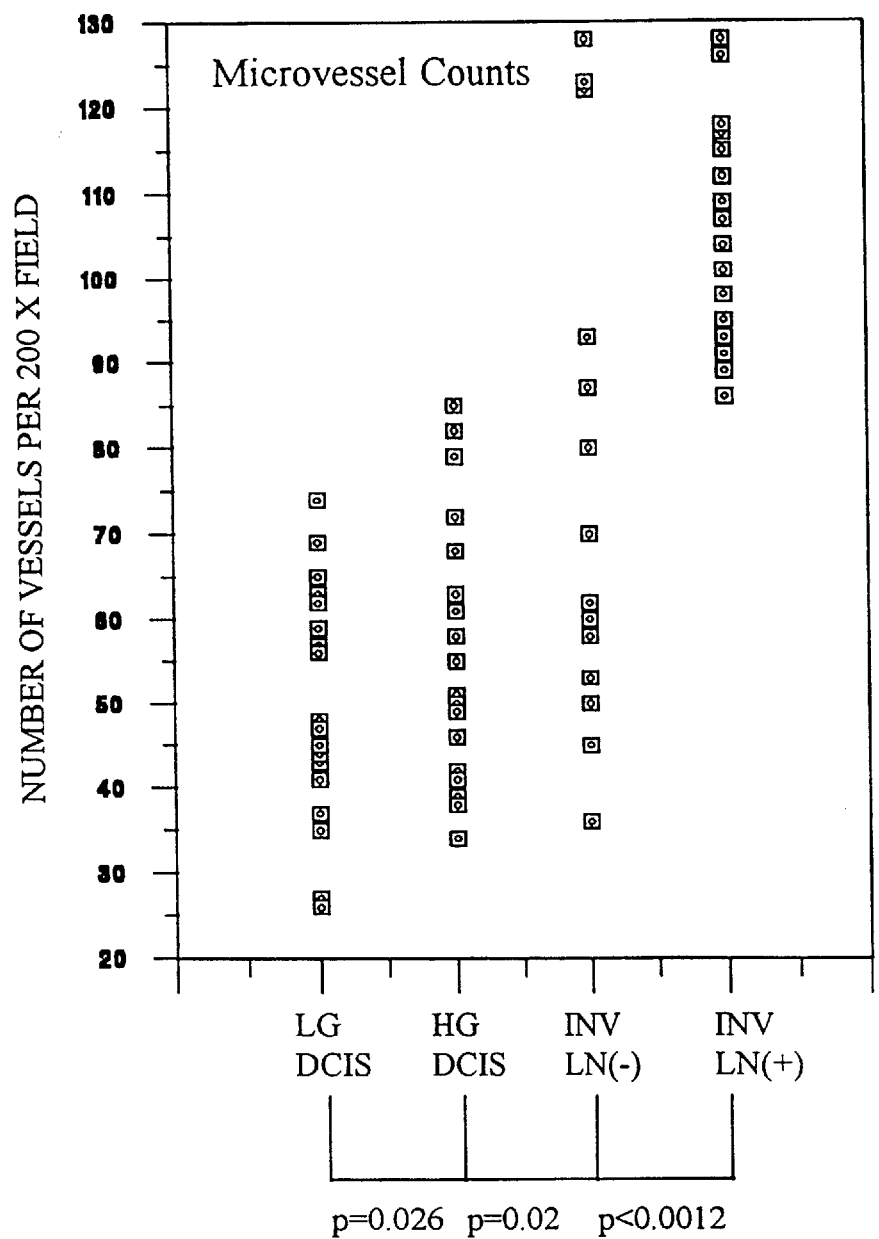

*p < 0.05 for paired one-tailed t-test, comparing the designated group with the group immediately above it in the Table
[1]ductal carcinoma in situ
[2]lymph node negative
[3]lymph node positive These results demonstrated that nuclear localization of p53, decreased thrombospondin 1 expression, and increased microvascularization were significantly correlated with increased invasiveness of primary breast cancer, increased metastasis, and poorer prognosis for breast cancer patients whose tumors had these markers. To determine whether disease progression was linked not only to the incidence, but also the degree of marker expression as well, the intensity of staining of the markers as determined above by immunohistochemistry or image analysis was plotted versus tumor histology for the four histological subsets described above. These results are shown in FIGS. 1A through 1C. These results demonstrate a distinct pattern of differences in intensity and degree of expression of the three tumor markers assayed above. These results show that nuclear p53 accumulation and the number of tumor microvessels increased in both the transition from low-grade DCIS to high-grade DCIS, and also in the transition from invasive tumors without evidence of metastatic spread to invasive tumors having metastasis-positive lymph node involvement (FIGS. 1A and 1B). TSP-1 expression showed a significant decline in intensity between high-grade DCIS and invasive cancer prior to metastatic spread.

Figure 2:
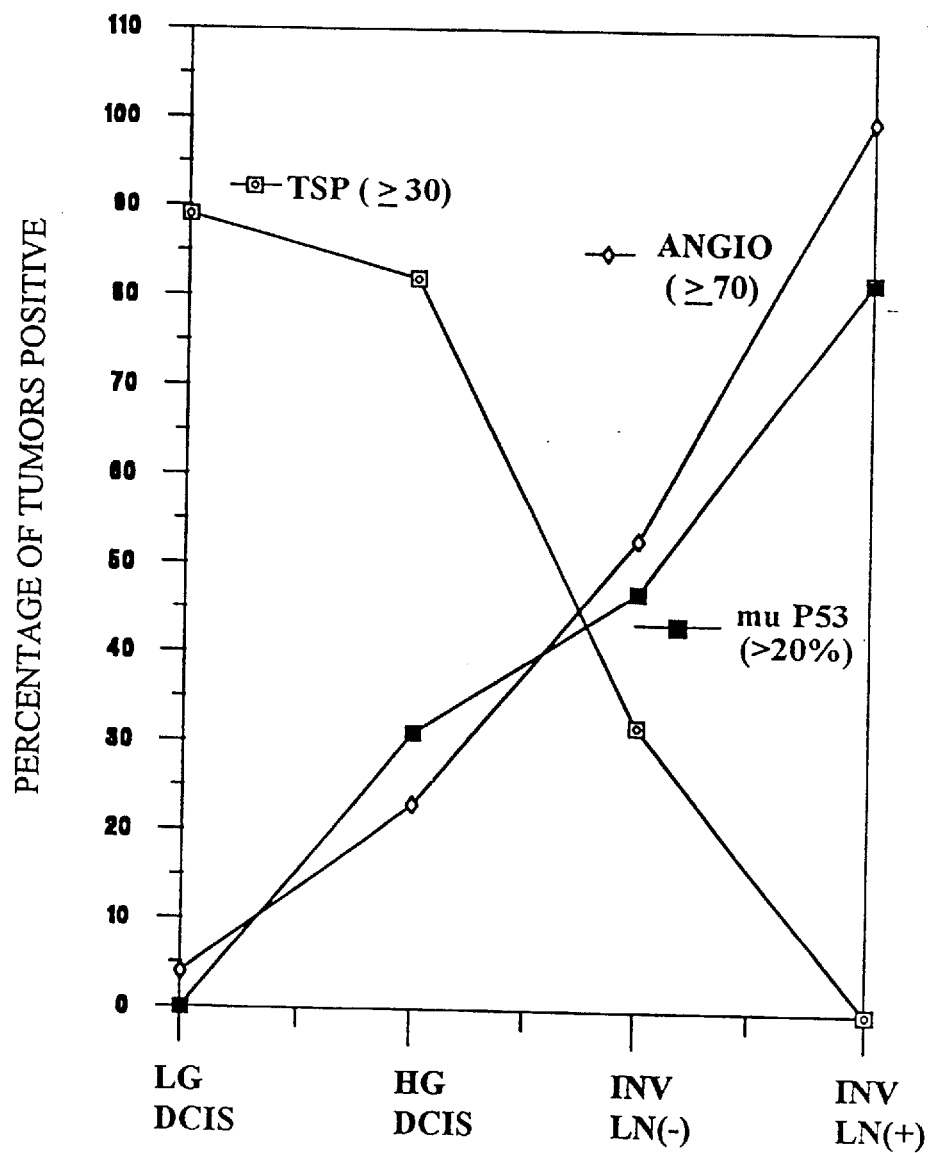
FIG. 2 is a graph showing the increase in p53 nuclear accumulation and microvascularization and decrease in TSP-1 expression with tumor progression for a cohort of breast cancer samples as described in Example 1.

These results are also shown graphically in FIG. 2, where the increase in p53 nuclear accumulation and microvascularization and decrease in TSP-1 expression with tumor progression is shown. These data suggest that a coordinated relationship existed between nuclear p53 accumulation and angiogenesis, while TSP-1 expression was inversely correlated with these two factors. Invasion and metastasis in breast cancer were associated in a statistically-significant way with acquisition of dysfunctional p53 (as evidenced by nuclear accumulation), decreased TSP-1 expression, and increased angiogenesis.

EXAMPLE 2

Tumor Prognostic Index

The results obtained in the assays described in Example 1 above were used to construct a prognostic (risk) index relating tumor progression and increasingly poorer disease prognosis with positive marker results, graded by intensity of immunohistochemical staining of each of the tumor markers.

The IHC scores obtained in Example 1 were used to construct a tumor progression/prognosis (risk) index as follows. Scores for each of the markers were associated with a integer index scale from +1 to −4. This index scale was constructed for each marker based on the following IHC staining results as follows. The p53 nuclear accumulation score was derived from the percentage of cell staining with anti-p53 antibody multiplied by (1+intensity of staining), using the intensity of staining and positive control cells described in Example 1. The TSP-1 score was derived from IA data obtained as described in Example 1, as weighted based on the percentage of cells staining positively for TSP-1. Angiogenesis was scored as greatest number of microvessels per field stained with anti-CD31 antibody, after a minimum scan of 10 fields. These scores and their associated weighted index scores are described below in Table III.

TABLE III p53, TSP-1 and Angiogenesis Indices

| Index | p53 Score | Thrombospondin Score | Microvascularization Score |
|---|---|---|---|
| 1 | 0–30 | >30 | 0–30 |
| 0 | 31–60 | 25–29 | 31–70 |
| −1 | 61–90 | 20–24 | 71–85 |

TABLE III-continued p53, TSP-1 and Angiogenesis Indices

| Index | p53 Score | Thrombospondin Score | Microvascularization Score |
|---|---|---|---|
| −2 | 91–120 | 15–19 | 86–100 |
| −3 | 121–150 | 10–14 | 101–123 |
| −4 | >150 | 0–9 | >123 |

The tumor prognosis (risk) index is then prepared by the sum of the index scores for p53 accumulation, TSP-1 expression and angiogenesis (microvascularization), with poor prognosis being determined for tumors having an summed index score of −5 or less.

The efficacy the prognostic (risk) index was assessed using Log rank tests on survival versus index score. The significance of the index scores on survival are shown in Table IV. In this table, it can be seen that a statistically-significant difference was observed in survival between patients having tumors with a summed index score $\geq -5$ when compared with patients having tumors with a summed index score $\leq -6$. Similarly, a statistically-significant difference was observed in survival between patients having tumors with a summed index score $\geq -6$ when compared with patients having tumors with a summed index score $< -7$. Finally, there was a statistically-significant difference was observed in survival between patients having tumors with a summed index score −7 when compared with patients having tumors with a summed index score $< -8$.

TABLE IV

Log Rank Tests to Compare Survival

| Index Score | Log Rank Test P Value |
|---|---|
| $\geq -5$ vs. $< -6$ | $p < 0.0001$ |
| $\geq -6$ vs. $< -7$ | $p < 0.0007$ |
| $\geq -7$ vs. $< -8$ | $p < 0.0548$ |

Figure 3A:
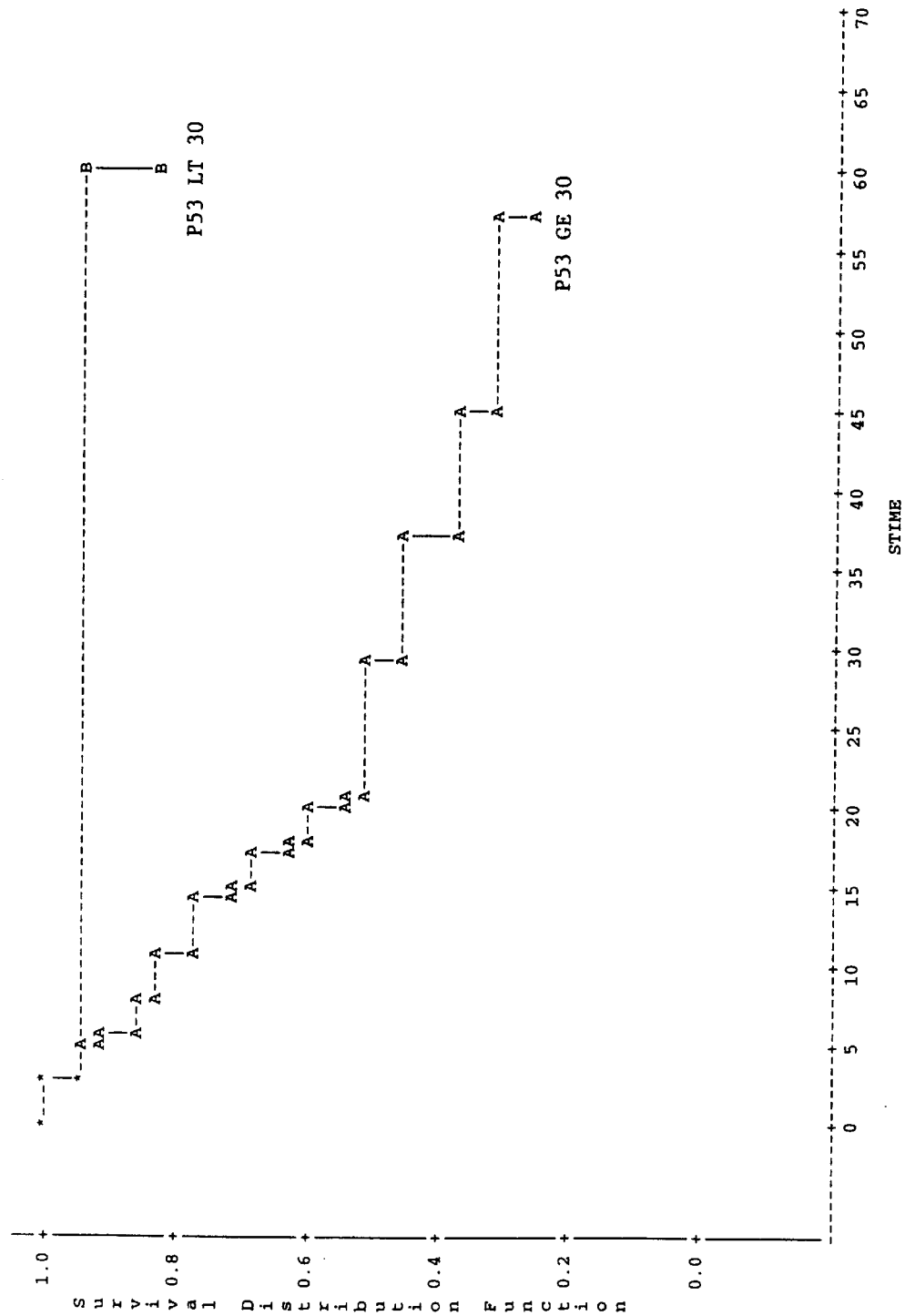
FIGS. 3A and 3B are graphs of a retrospective study of patient survival of 40 breast cancer patients as described in Example 2, comparing patients having a prognostic risk index of greater than or equal to −5 (GE −5 FIG. 3A) with patients having a prognostic risk index of less than −6 (LE −6 FIG. 3B).
Figure 3B:
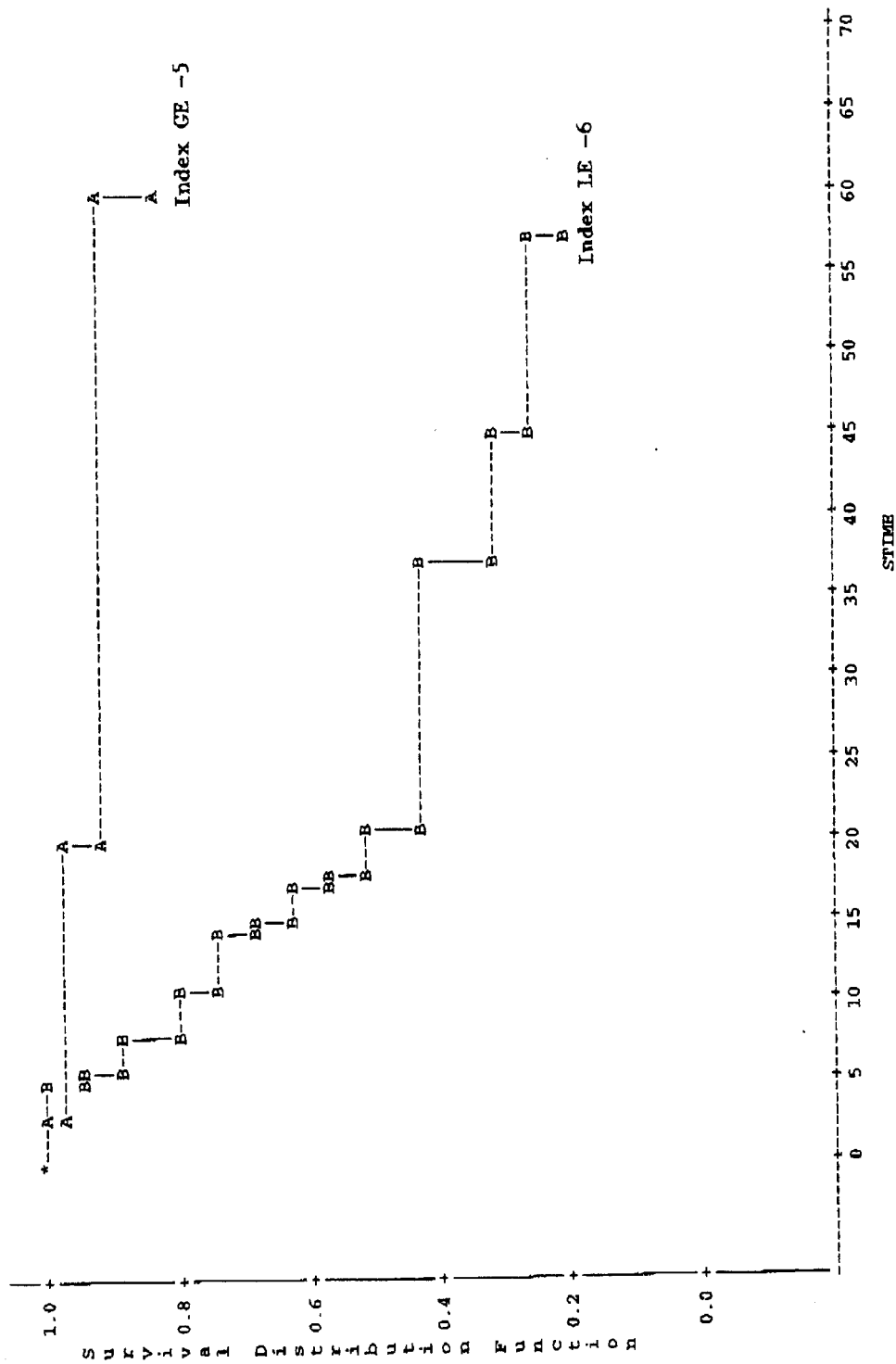

These results are shown graphically in FIG. 3 in a retrospective analysis of 40 breast cancer patients having a sununed prognostic (risk) index score greater than −5 (GE −5) or less than −6 (LE −6). In this study, survival was correlated with risk index scores greater than or equal to −5 (about 80% survival at 60 months post-diagnosis) versus about 20% survival for patient having tumors with index scores less than −6.

These results were also analyzed using multivariate analysis including angiogenesis, tumor size and lymph node status. These results showed that the index was more predictive of patients' prognosis for survival than the commonly-used indices of tumor size or lymph node status.

These results demonstrate that the tumor progression index is a statistically reliable predictor of tumor prognosis and disease progression for breast cancer.

EXAMPLE 3

Tumor Progression/Prognosis Analysis for Prostate Cancer

The immunohistochemical analyses described above in Example 1 were applied to prostate cancer samples. In addition, androgen receptor expression was assayed for these tumors, due to the recognized correlation between androgen receptor expression and poor prognosis/survival in these patients.

In this study, 104 prostate cancer patient tumor samples were assayed for nuclear accumulation of p53, TSP-1 expression, androgen receptor (AR) gene expression and microvascularization. These assays were performed immunohistochemically as described above in Example 1, except that androgen receptor expression was determined using an anti-AR antibody (Biogenics, used at 1:20 dilutions).

The results of these studies closely paralleled the results obtained with breast carcinoma, and the indices derived from the p53, TSP-1 and angiogenesis/microvascularization data were identical to those shown in Table III. In addition, AR expression was found to be negatively correlated with prognosis and survival using multivariate analysis (Cox regression analysis), which showed statistical significance (p=0.0077). Interestingly, the presence of nuclear accumulation of p53 was correlated with AR expression (p<0.0041).

The risk index incorporating levels of nuclear p53, TSP-1 expression and angiogenesis was found to be significantly associated with survival. Survival in patients with a risk index of −8 or less was significantly lower than that in patients with a prognostic (risk) index of −7 or greater (p<0.0001). The risk index was also associated with survival (p<0.0061) even after adjustment for age and stage.

Figure 4:
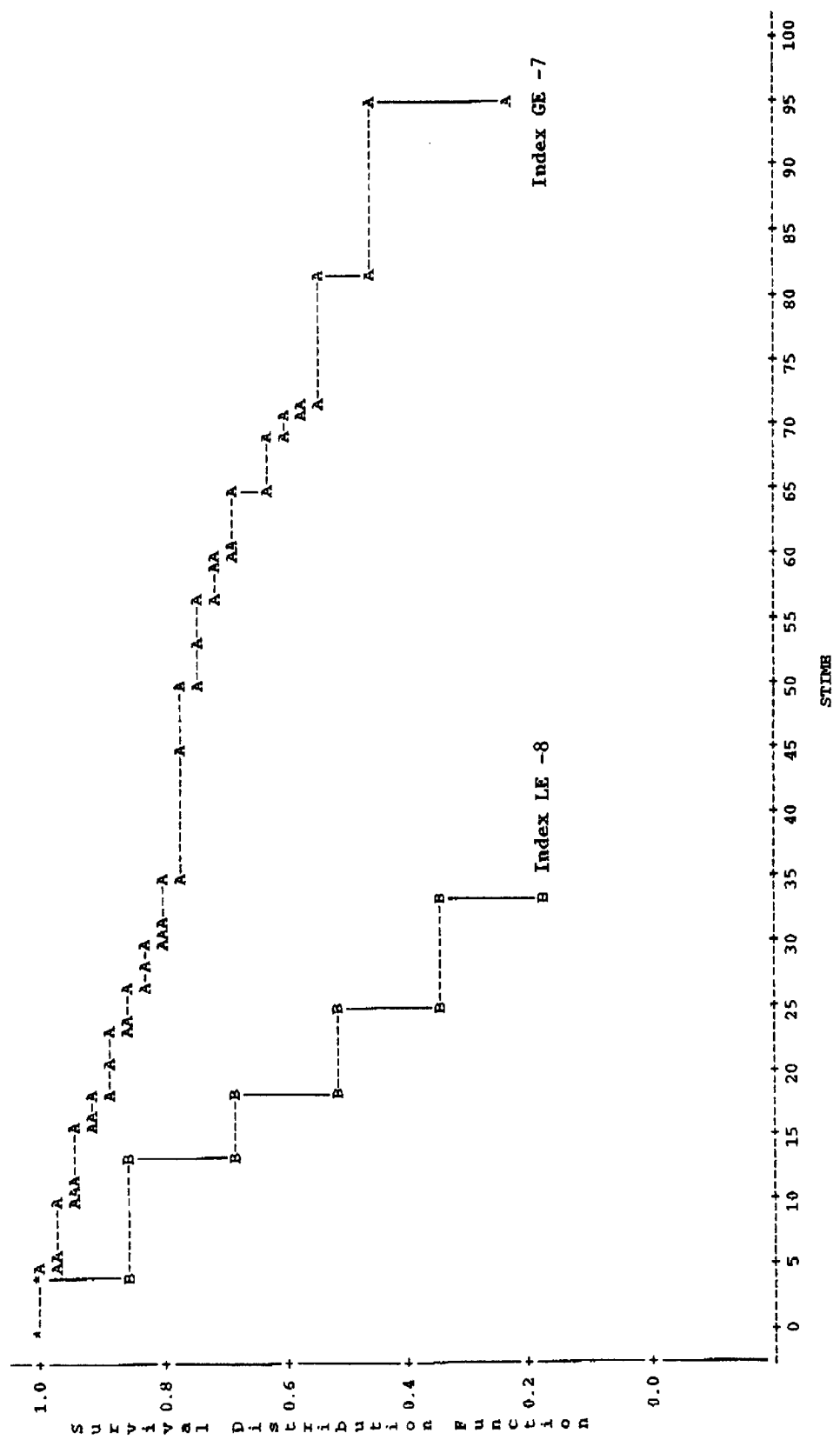
FIG. 4 is a graph of a retrospective study patient survival of 104 prostate cancer patients as described in Example 3, comparing patients having a prognostic risk index of greater than or equal to −7 (GE −7) with patients having a prognostic risk index of less than −8 (LE −8).

These results are shown graphically in FIG. 4. This Figure illustrates the results of a retrospective analysis of 104 prostate cancer patients having a summed prognostic (risk) index score greater than −7 (GE −7) or less than −8 (LE −8). In this study, survival was correlated with risk index scores greater than or equal to −7 (about 95 months to 20% survival post-diagnosis) versus about 30 months to 20% survival post-diagnosis for patients having tumors with index scores less than −8. These results demonstrated that the prognosis (risk) index was reliable for predicting poor prognosis/increased disease progression based on the tested tumor markers.

It should be understood that the foregoing disclosure emphasizes certain specific embodiments of the invention and that all modifications or alternatives equivalent thereto are within the spirit and scope of the invention as set forth in the appended claims.

We claim:

1. A method for determining the prognosis of cancer patients for metastasis, recurrence and relapse of neoplastic disease comprising the steps of
    (a) obtaining a tumor sample from a human cancer patient;
    (b) determining the level of p53 nuclear localization, the level of thrombospondin 1 expression and the extent of microvascularization in the tumor sample by immunohistochemical staining;
    (c) preparing an index comprising index values of
        (i) the percentage of cells in the tumor sample that are positive for p53 nuclear localization multiplied by the sum of (one plus the intensity of immunohistochemical staining);
        (ii) the greatest number of microvessels per 200× magnification field, after a minimum scan of ten fields; and
        (iii) the percentage of cells in the tumor sample that are positive for thrombospondin 1 expression;
    wherein the intensity of p53 staining is assigned
        a value of 0 for staining equal to a negative control,
        a value of 1 for staining greater than the negative control,
        a value of 2 for moderate staining intensity which is more than the negative control, but less than the positive control,
        a value of 3 for staining intensity equal to a positive control, and
        a value of 4 for staining intensity greater than the positive control;
    wherein positive p53 nuclear localization is determined by more than 5% of the cells stained at an intensity of 2 or greater; and
    wherein positive thrombospondin 1 expression is determined by greater than 30 optical density units;
    (d) weighing the index values of steps (c)(i), (c)(ii) and (c)(iii) on a scale of +1 to −4, to yield weighed values, with low p53 nuclear localization, high thrombospondin 1 expression and low level of microvascularization, each, being scored as +1; and
    (e) summing the weighed values for p53 nuclear localization, thrombospondin 1 expression and microvascularization;
    wherein the prognosis for metastasis, recurrence and relapse of neoplastic disease is made when the sum of the weighed values is less than −5 but greater than or equal to −12.

2. The method of claim 1 wherein the cancer is breast cancer.

3. The method of claim 1 wherein the cancer is prostrate cancer.

4. The method of claim 1 wherein the prognosis is made when the sum of the weighed values is less than −5, less than −6, less than −7 or less than −8.

* * * * *